United States Patent
Persen et al.

(10) Patent No.: US 10,980,433 B2
(45) Date of Patent: Apr. 20, 2021

(54) HEALTH MONITORING AND GUIDANCE

(71) Applicant: Livmor, Inc., Irvine, CA (US)

(72) Inventors: Ken Persen, Dove Canyon, CA (US); Ross Grady Baker, Jr., Bellaire, TX (US)

(73) Assignee: LIVMOR, INC., Irvine, CA (US)

( * ) Notice: Subject to any disclaimer, the term of this patent is extended or adjusted under 35 U.S.C. 154(b) by 91 days.

(21) Appl. No.: 16/362,527

(22) Filed: Mar. 22, 2019

(65) Prior Publication Data

US 2019/0290147 A1    Sep. 26, 2019

Related U.S. Application Data

(63) Continuation-in-part of application No. 16/035,568, filed on Jul. 13, 2018, now abandoned.

(Continued)

(51) Int. Cl.
| | | |
|---|---|---|
| A61B 5/024 | (2006.01) | |
| A61B 5/00 | (2006.01) | |
| A61B 5/11 | (2006.01) | |
| A61B 5/0205 | (2006.01) | |
| A61B 5/145 | (2006.01) | |

(52) U.S. Cl.
CPC ........ *A61B 5/02416* (2013.01); *A61B 5/0006* (2013.01); *A61B 5/02405* (2013.01); *A61B 5/1118* (2013.01); *A61B 5/681* (2013.01); *A61B 5/0205* (2013.01); *A61B 5/14532* (2013.01)

(58) Field of Classification Search
CPC ..... A61B 2562/00; A61B 5/0006; A61B 5/01; A61B 5/0205; A61B 5/02405; A61B 5/02416; A61B 5/0816; A61B 5/1118; A61B 5/145; A61B 5/14532; A61B 5/165; A61B 5/681; A61B 5/7207; A61B 5/7235;

(Continued)

(56) References Cited

U.S. PATENT DOCUMENTS

| | | | |
|---|---|---|---|
| 9,980,678 B2 * | 5/2018 | Chan | ............... A61B 5/0456 |
| 10,499,850 B2 * | 12/2019 | Fuerst | ............ A61B 5/0022 |

(Continued)

OTHER PUBLICATIONS

Kikillus, N., et al., Three Different Algorithms for Identifying Patients Suffering from Atrial Fibrillation during Atrial Fibrillation Free Phases of the ECG; Computers in Cardiology 2007, vol. 34, pp. 801-804.

International Search Report and Written Opinion dated Sep. 4, 2019, for related international application No. PCT/US2019/024668.

Meredith, D. J., et al.. Photoplethysmographic derivation of respiratory rate: a review of relevant physiology; Journal of Medical Engineering & Technology. 2012. pp. 1-8.

(Continued)

*Primary Examiner* — Jonathan T Kuo
(74) *Attorney, Agent, or Firm* — Pillsbury Winthrop Shaw Pittman LLP

(57) ABSTRACT

A photoplethysmographic (PPG) signal communicated by a PPG sensor of a wearable device worn by a user may be received by a processor. The processor may detect a plurality of heartbeats of the user from the PPG-signal, determine a heart rate of the user based on at least the plurality of heartbeats, determine a heart rate variability (HRV) based on the plurality of heartbeats, determine a respiration rate of the user based on a low frequency component of the PPG signal, and determine whether the user is in a stressed state based on the heart rate, the HRV, and the respiration rate. The processor may cause the display of information related to the stress state of the user, and instructions and/or advice for reducing a stress level of the user.

34 Claims, 10 Drawing Sheets

Related U.S. Application Data

(60) Provisional application No. 62/535,391, filed on Jul. 21, 2017.

(58) Field of Classification Search
CPC ....... G04G 21/00–21/025; G16H 50/00–50/80
USPC ..................... 361/679.01–679.03; 368/10–14
See application file for complete search history.

(56) References Cited

U.S. PATENT DOCUMENTS

| | | | |
|---|---|---|---|
| 10,709,339 | B1 | 7/2020 | Lusted |
| 2004/0015091 | A1 | 1/2004 | Greenwald |
| 2007/0100666 | A1* | 5/2007 | Stivoric .................. A61B 5/01 705/3 |
| 2014/0221845 | A1 | 8/2014 | Mestha |
| 2016/0302677 | A1* | 10/2016 | He ..................... A61B 5/02125 |
| 2016/0338640 | A1* | 11/2016 | Chan ........................ A61B 5/08 |
| 2016/0361023 | A1* | 12/2016 | Martin .................. A61B 5/1118 |
| 2018/0116607 | A1 | 5/2018 | Yu |
| 2018/0220957 | A1* | 8/2018 | Fuerst .................. A61B 5/0022 |

OTHER PUBLICATIONS

Pirhonen, Mikko, et al.. Acquiring Respiration Rate from Photoplethysmographic Signal by Recursive Bayesian Tracking of Intrinsic Modes in Time-Frequency Spectra; BioMediTech Institute and Faculty of Biomedical Sciences and Engineering, Tampere University of Technology. May 24, 2018. pp. 1-16.

Park, Chanki and Boreom Lee. Real-time estimation of respiratory rate from a photplethysmogram using an adaptive lattice notch filter. BioMedical Engineering OnLine. 2014. 13:170. pp. 1-18.

Sioni, Riccardo and Luca Chittaro. Stress Detection Using Physiological Sensors. Physiological Computing. Oct. 2015. pp. 26-33.

Roscoe, A.H.. Assessing pilot workload. Why measure heart rate, HRV and respiration? Biological Psychology. 34. (1192) pp. 259-287.

International Search Report and Written Opinion dated Jun. 5, 2019, for corresponding international application No. PCT/US2019/023717.

International Preliminary Report on Patentability and Written Opinion dated Oct. 8, 2020, for related International Application No. PCT/US2019/024668.

* cited by examiner

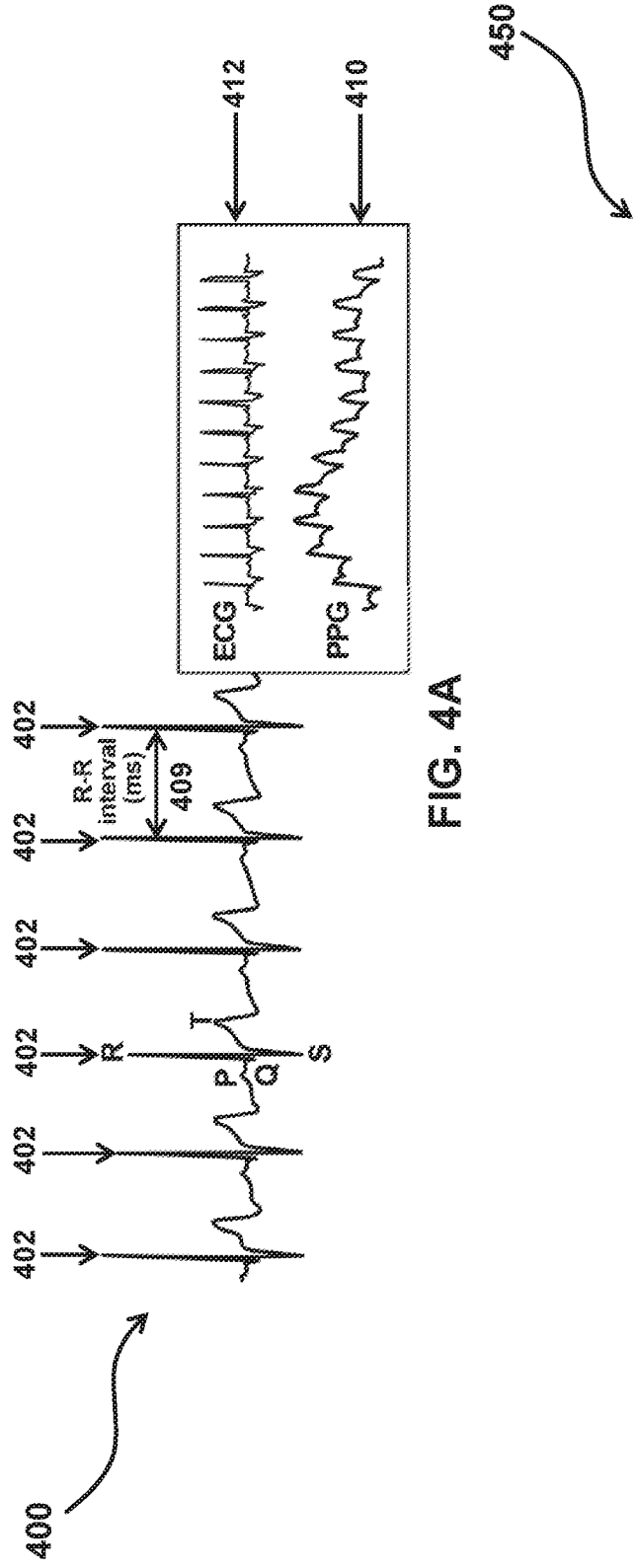
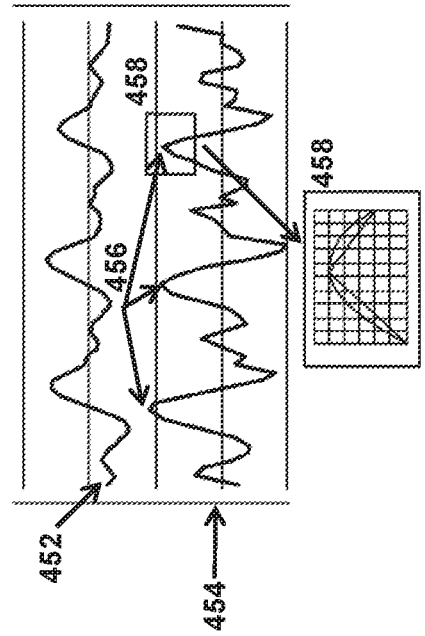
FIG. 4A
FIG. 4B

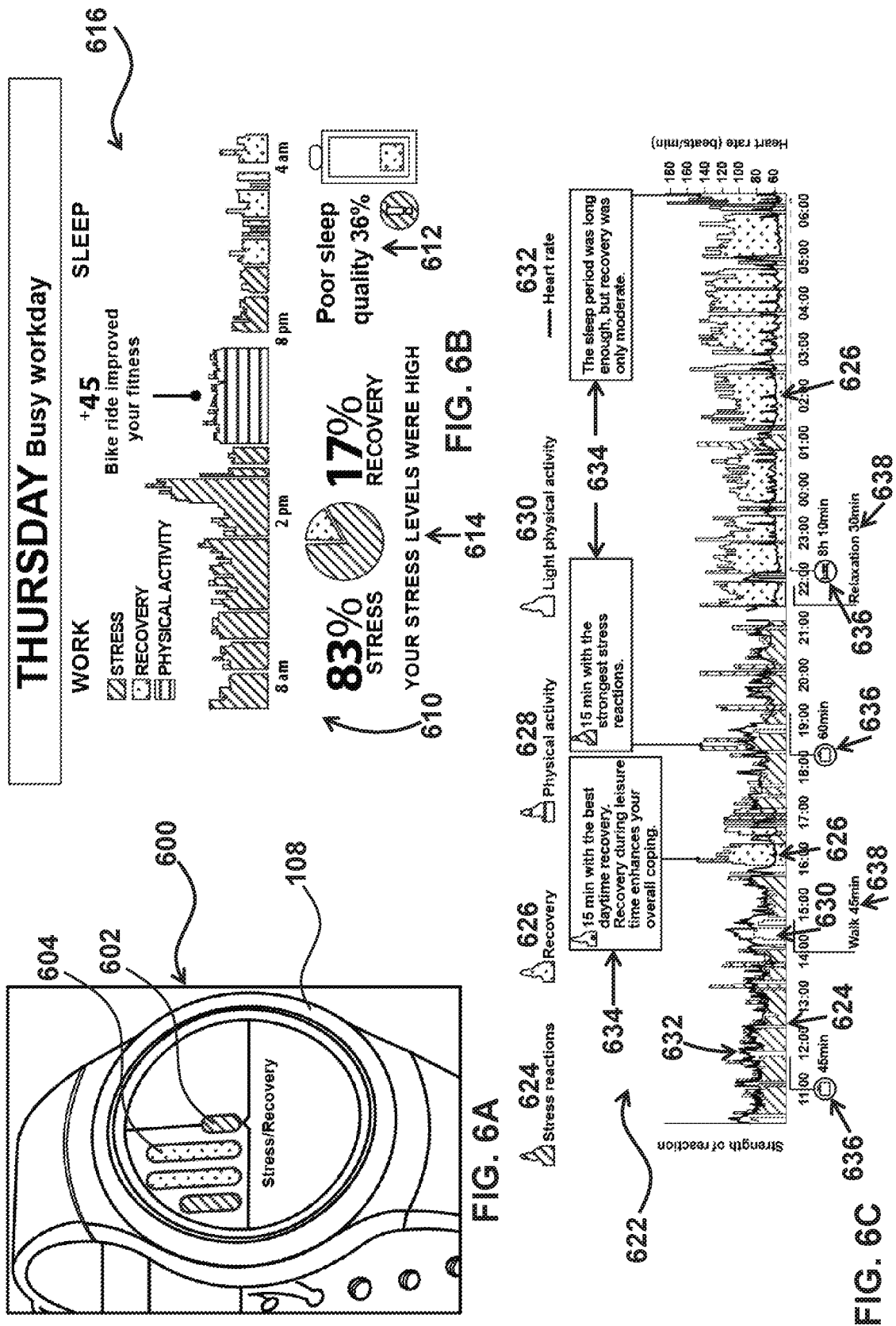

HEALTH MONITORING AND GUIDANCE

RELATED APPLICATION(S)

This application claims priority to and the benefit of U.S. patent application Ser. No. 16/035,568, filed Jul. 13, 2018, titled "Systems and Methods for Health Monitoring and Guidance," which claims priority to U.S. Provisional Patent Application No. 62/535,391, filed Jul. 21, 2017, both of which are hereby incorporated by reference in their entirety.

DESCRIPTION OF THE RELATED ART

Disclosures herein relate to monitoring the health of a user and providing health guidance. For example, electrical and physiological characteristics of a user's human heart can be measured using sensors such as electrocardiogram (ECG) sensors or photoplethysmograph (PPG) sensors. In some circumstances, such sensors may be included on a wearable device such as a smartwatch. Signals from such sensors may then be analyzed to determine useful and informative health states of a patient, such as heart rates, heart rate variability, particular heart rhythms, and the like.

SUMMARY

Systems, methods and computer software for monitoring the heath of a user are disclosed herein. In one implementation, a computer program product is described comprising a non-transitory, machine-readable medium storing instructions which, when executed by a processor, may cause the processor to perform operations such as receiving a photoplethysmographic (PPG) signal communicated by a PPG sensor of a wearable device worn by a user, detecting a plurality of heartbeats of the user based on the PPG-signal, determining a heart rate of the user based on at least the plurality of heartbeats, determining a heart rate variability (HRV) of the user based on the plurality of heartbeats, determining a respiration rate of the user based on a low frequency component of the PPG signal, and determining whether the user is in a stressed state based on the heart rate, the HRV, and the respiration rate.

In some implementations, determining whether the user is in a stressed state based on the heart rate, the HRV, and the respiration rate may comprise determining a mathematical model for the user, causing the heart rate, the HRV, and the respiration rate to be used as inputs into the mathematical model, and causing the mathematical model to output the determination of whether the user is in a stressed state based on the inputs. In some implementations, the mathematical model may comprise a weighted combination of the heart rate, the respiration rate, and the HRV for the user. The heart rate may be weighted more heavily than the respiration rate or the HRV.

In certain implementations, the weighted combination of heart rate, respiration rate, and heart rate variability may comprise a three feature vector and causing the mathematical model to output the determination of whether the user is in a stressed state may comprise analyzing the three feature vector in a three dimensional vector space to determine whether the three feature vector breaches one or more thresholds that define one or more stress zones or volumes in the three dimensional vector space. The mathematical model may be configured such that, responsive to at least a portion of the three feature vector passing through and/or being bounded by the one or more stress zones or volumes, the mathematical model determines that the user is in a stressed state.

In some implementations, the operations performed by the programmable processor may further comprise causing the display of information related to the determination of whether the user is in a stressed state on a display of a wearable device and/or on a different computing device associated with the user. In some implementations, the operations may further include making multiple determinations of whether the user is in a stressed state over a period of time.

In additional implementations, the operations may further include receiving a motion signal communicated by an accelerometer on the wearable device worn by a user during a period of time. The motion signal may convey information related to an activity level of the user. In some implementations, the operations performed by the programmable processor may further including determining whether the activity level is indicative of sleep, exercise, and/or normal daily activity; and causing the display of periods of stress, sleep, exercise, and/or normal daily activity for the period of time.

In additional implementations, the operations performed by the programmable processor may further comprise (responsive to a determination that the user is in a stressed state) determining breathing guidance and causing display of the breathing guidance to the user on a display of the wearable device, to facilitate stress reduction.

As another example, a wrist worn device configured to determine whether a user is in a stressed state is described. The wrist worn device may comprise a photoplethysmographic (PPG) sensor, at least one programmable processor and a non-transitory storage medium, a user interface, and/or other components. The PPG sensor may be configured to generate a PPG signal. The non-transitory, machine-readable medium may store instructions which, when executed by the at least one programmable processor, cause the programmable processor to perform operations comprising: receiving, at the at least one programmable processor, the PPG signal communicated by the PPG sensor, detecting a plurality of heartbeats of the user based on the PPG-signal, determining a heart rate of the user based on at least the plurality of heartbeats, determining a heart rate variability (HRV) of the user based on the plurality of heartbeats, determining a respiration rate of the user based on a low frequency component of the PPG signal, and determining whether the user is in a stressed state based on the heart rate, the HRV, and the respiration rate. The user interface may be controlled by the programmable processor to display information related to the determination of whether the user is in a stressed state.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings, FIG. 4A illustrates example heartbeat interval data in accordance with certain aspects of the present disclosure, FIG. 4B illustrates an example method for heartbeat detection in accordance with certain aspects of the present disclosure, FIG. 6A illustrates a first example of a health information display of a user wearable device application and/or a communication device application in accordance with certain aspects of the present disclosure, FIG. 6B illustrates a second example of a health information display of a user wearable device application and/or a communication device application in accordance with certain aspects of the present disclosure, FIG. 6C illustrates a third example of a health information display of a user wearable device application and/or a communication device application in accordance with certain aspects of the present disclosure.

DETAILED DESCRIPTION

The subject matter described herein relates to systems, methods and software for monitoring certain heath states of a user and for providing the user with guidance. Exemplary systems are described that can utilize information from sensors to assess various aspects of user's health, for example, by analyzing relationships between heart rate, respiration rate, heart rate (and/or pulse rate) variability, and/or other parameters.

The present systems can be configured to determine levels of stress experienced by a user and to provide guidance that may facilitate a reduction in the user's level of stress. For example, if a user observes (or is alerted to) the occurrence of prolonged periods of stress, the user can be provided with breathing exercises to reduce stress—potentially preventing deterioration of the user's health. In some implementations, the present systems can be configured to monitor respiration rate, heart rate, HRV/PRV and/or other parameters to assess the effectiveness of the breathing exercises and to present feedback to the user so he or she can see the immediate effect of the exercises on his or her current level of stress and physiology. This can provide a positive feedback mechanism that may encourage the user to continue the exercises as they can directly and quantifiably see the effect on their physiology.

Figure 1:
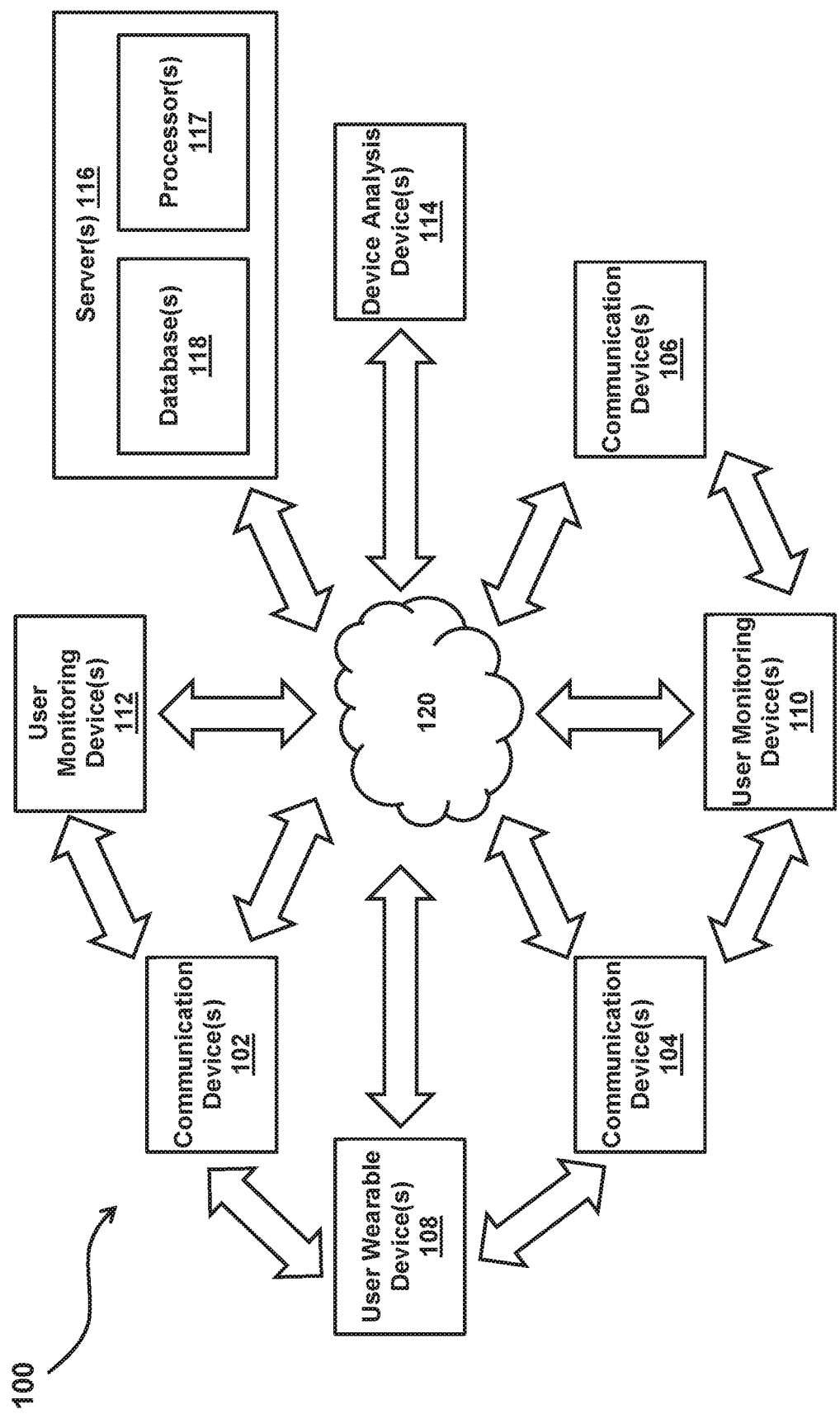
FIG. 1 illustrates an exemplary system that can provide for the monitoring of user health characteristics and provide health-related guidance in accordance with certain aspects of the present disclosure.

FIG. 1 illustrates an exemplary system 100 that can provide for the monitoring of health characteristics of a user (for example, a human patient, or other living organism) and can provide health guidance to the user based on the health characteristics monitoring.

In some implementations, the exemplary system 100 depicted in FIG. 1 may include elements such as user wearable device(s) 108 (e.g., a smartwatch), communication devices 102, 104, and 106 (e.g., a mobile phone or PC), user monitoring devices 110 and 112 (e.g., a separate smart scale or blood glucose monitor), data analysis device(s) 114, server(s) 116 (e.g., including processor(s) 117 and database(s) 118), network(s) 120, and/or other components. The server(s) 116, wearable devices 108, communication devices 102-106, user monitoring devices 110 and 112, data analytics devices 114 and/or other devices may include communication lines or ports to enable the exchange of information within a network (e.g., network 120), or within other computing platforms via wired or wireless techniques (e.g., Ethernet, fiber optics, coaxial cable, WiFi, Bluetooth, near field communication, or other technologies).

It should be noted that, while one or more operations are described herein as being performed by particular components of system 100, those operations may, in some implementations, be performed by other components of system 100. As an example, while one or more operations are described herein as being performed by components of data analysis device(s) 114, those operations may, in other implementations, be performed by components of the user wearable device(s) 108, by components of the communications devices 102, 104, and 106, and/or by other components of system 100. In addition, although many of the devices are shown separately, one or more components shown in FIG. 1 may be included in and/or coupled to one more other components shown in FIG. 1. For example, one or more data analysis devices 114 may be included in one or more servers 116, one more communication devices 102-106, one or more user monitoring devices 110 and/or 112, one or more user wearable devices 108, and/or other components.

The user wearable device(s) 108 may be a smartwatch (for example, Samsung Gear, Apple Watch, etc.), or any other device that a user can wear. A user wearable device 108 may include one or more sensors that are housed by and/or otherwise integrated with the device. For example, a user wearable device 108 that is a smartwatch may include motion sensors (for example, accelerometers), bio-impedance sensors, electrocardiogram (ECG) sensors, ballistocardiogram sensors, acoustic sensors (for example, ultrasound sensors), photo plethysmographic (PPG) sensors that can use light-based technology to sense a rate of blood flow, and other sensors. The PPG sensor may be configured to generate a PPG signal and communicate the PPG signal to at least one programmable processor of wearable device 108 worn by a user, for example. Wearable device 108 may also be considered herein to include sensors that are worn on a user's body but not integrated within the main wearable portion (for example, an ECG sensor worn on a user's chest that is not integrated with a smartwatch, but which nevertheless communicates with the smartwatch).

Figure 2:
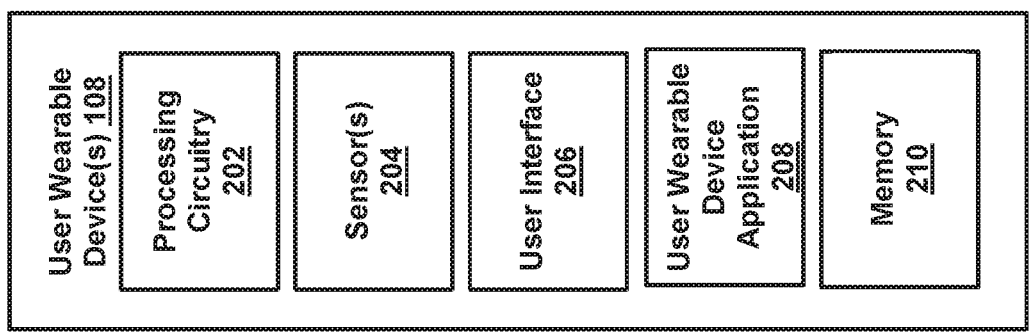
FIG. 2 illustrates an implementation of a user wearable device in accordance with certain aspects of the present disclosure.

FIG. 2 illustrates wearable device 108, including processing circuitry 202, sensor(s) 204, wearable user interface 206, wearable device application 208, and memory 210. As noted, sensor(s) 204 may include multiple sensors integrated with the main wearable portion of the device and/or sensors located elsewhere on the user's body. The wearable device application 208, and signals from sensor(s) 204, may be stored in memory 210.

Wearable user interface 206 is configured to provide an interface between user wearable device 108 and/or system 100 (FIG. 1) and a user through which the user may provide information to and receive information from user wearable device 108 and/or system 100. This enables data, cues, results, and/or instructions and any other communicable items, collectively referred to as "information," to be communicated between a user and one or more of the components of system 100 shown in FIG. 1 and/or the components of wearable device 108 shown in FIG. 2. A user may interact with wearable user interface 206, for example, to enter data such as age, height, weight and gender, or to view measured or calculated metrics such as heart rate, pulse rate variability, stress level, breathing guidance, and the like. Examples of interface devices suitable for inclusion in user wearable user interface 206 comprise a keypad, buttons, switches, a display screen, a touch screen, speakers, a microphone, an indicator light, an audible alarm, a tactile feedback device, and/or other interface devices. In short, any technique for communicating information with system 100 is contemplated by the present disclosure as wearable user interface 206.

Wearable device application 208 may run on processing circuitry 202 and perform such operations as receiving signals from sensor(s) 204, calculating various health characteristics, outputting the display of information, providing health guidance to the user, etc. Wearable device application 208 and/or processing circuitry 202 are configured to provide information processing capabilities in wearable device 108 and/or system 100. Processing circuitry 202 may comprise one or more of a digital processor, an analog processor, and a digital circuit designed to process information, an analog circuit designed to process information, a state machine, and/or other mechanisms for electronically processing information. Although processing circuitry 202 is shown in FIG. 2 as a single entity, this is for illustrative purposes only. In some implementations, processing circuitry 202 may comprise a plurality of processing units. These processing units may be physically located within the same device (e.g., user wearable device 108), or processing circuitry 202 may represent processing functionality of a plurality of devices operating in coordination. In some implementations, processing circuitry 202 is configured to execute one or more computer program modules. In some implementations, wearable device application 208 may include the one more computer program modules (e.g., programming instructions configured to cause user wearable device 108 to function as described herein). Processing circuitry 202 may be configured to execute the modules by software; hardware; firmware; some combination of software, hardware, and/or firmware; and/or other mechanisms for configuring processing capabilities.

In some implementations, memory 210 comprises electronic storage media that electronically stores information. The electronic storage media of memory 210 may comprise one or both of system storage that is provided integrally (i.e., substantially non-removable) with a user wearable device 108 and/or removable storage that is removably connectable to a user wearable device 108 via, for example, a port (e.g., a USB port, a firewire port, etc.) or a drive (e.g., a disk drive, etc.). Memory 210 may comprise one or more of optically readable storage media (e.g., optical disks, etc.), magnetically readable storage media (e.g., magnetic tape, magnetic hard drive, etc.), electrical charge-based storage media (e.g., EPROM, RAM, etc.), solid-state storage media (e.g., flash drive, etc.), and/or other electronically readable storage media. Memory 210 may store software algorithms, information determined by processing circuitry 202 and/or application 208, information received from a user, and/or other information that enables system 100 to function properly. Memory 210 may be (in whole or in part) a separate component within a user wearable device 108, or memory 210 may be provided (in whole or in part) integrally with one or more other components of a user wearable device 108 (e.g., processing circuitry 202).

In some implementations, processing circuitry 202, wearable device application 208, memory 210, and/or other components may comprise a computer program product comprising a non-transitory, machine-readable medium storing instructions which, when executed by at least one programmable processor, cause the at least one programmable processor to perform various operations (e.g., as described below). The operations may comprise, for example, receiving, at the at least one programmable processor, the PPG signal communicated by the PPG sensor.

Wearable device 108 may be calibrated and/or otherwise configured (or reconfigured) during a calibration period. The calibration may be caused and/or performed by a user, processing circuitry 202, user wearable device application 208, and/or other components of system 100. For example, a user may wear device 108 for a 24-hour calibration period upon first use to allow for the collection of user information from sensor(s) 204. The collection of characteristics such as pulse rate or respiration rate over a period of time may facilitate device calibration and provide user information helpful in the future analysis of signals and the provision of health guidance to the user. In some implementations, the calibration may be performed while the user is wearing a single lead ECG or other sensor(s) for reference purposes.

Returning to FIG. 1, communication devices 102, 104, and 106 may include any type of mobile or fixed device, for example, a desktop computer, a notebook computer, a smartphone, a tablet, or other communication device. Users may, for instance, utilize one or more communication devices 102, 104, and 106 to interact with one another, with one or more wearable devices, one or more servers, or other components of system 100.

Figure 3:
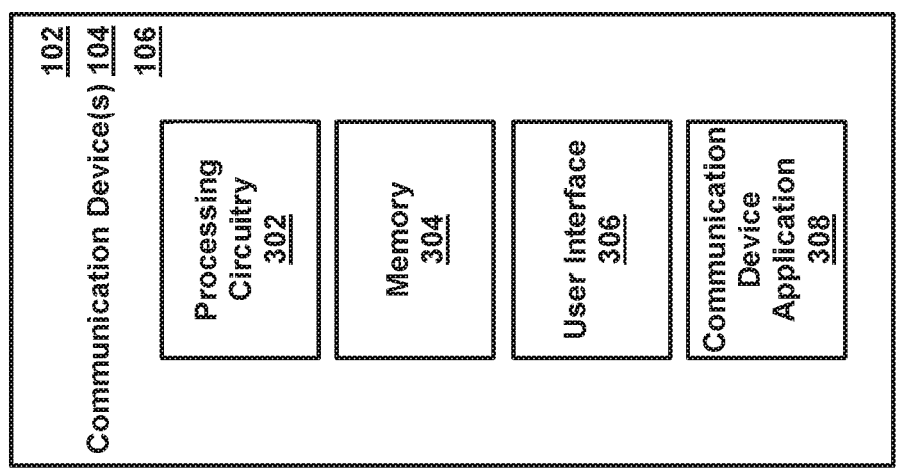
FIG. 3 illustrates an implementation of a communication device in accordance with certain aspects of the present disclosure.

FIG. 3 illustrates some components of an exemplary communication device 102, 104, and/or 106 including processing circuitry 302, memory 304, user interface 306, and communication device application 308. The processing circuitry 302, memory 304, and user interface 306 function similarly to the processing circuitry 202, memory 210, and user interface 206, respectively, in FIG. 2, although the application and user interface of a communication device will commonly have greater functionality than that of a wearable device.

In some implementations, communication device application 308 may be a mobile application (for example, a smartphone application), or a web application. The communication device application 308, in some implementations, can communicate with the user wearable device application 208 via Bluetooth (or any other method of wired or wireless communication) and/or may transmit measurements for archival and post-processing to a cloud-based database (for example, database(s) 118). The communication device application 308 may aggregate data from the other sensors (for example, from user monitoring devices 110 and 112), perform pre-transmission processing locally, and transmit data for further processing or viewing. In some implementations, processing circuitry 302, communication device application 308, memory 304, and/or other components may comprise a computer program product comprising a non-transitory, machine-readable medium storing instructions which, when executed by at least one programmable processor, cause the at least one programmable processor to perform various operations (e.g., as described below).

Returning to FIG. 1, in some implementations, user monitoring devices 110 and 112 may include a blood pressure monitoring device (for example, a blood pressure cuff), a weight monitoring device (for example, a scale), a blood glucose monitoring device, etc. User monitoring devices 110 and 112 may measure health states of the user different from the health states measured by user wearable device(s) 108.

The health monitoring and guidance systems and methods detailed herein typically utilize signals coming from one or more sensors that may be in contact with a user's body and that are sensing information relevant to the user. Sensors can be integrated with a wearable device (e.g., a wearable device 108), communicating with a wearable device, or can instead be separate from a wearable device and communicating with system 100 through other components.

As discussed further herein, system 100 can include components and methods for acquiring particular signals, for processing such signals (e.g., providing noise reduction), and for modifying signal acquisition methods. Each of these activities may be performed by a variety of the components of system 100.

In some implementations, a user wearable device 108 may receive an optical signal such as a pulse signal from optical sensor(s) (e.g., sensors 204 in FIG. 2) utilizing, for example, green and/or infrared wavelengths of light. Wearable device 108 may include and/or be operatively coupled with an optical PPG sensor (e.g., a first sensor 204) configured to generate output signals conveying information related to the heart rate of a user.

Wearable device 108 may also include a sensor to capture a motion signal that may be used to assess noise or interference resulting from motion of a user wearing device 108 or to assess other parameters relevant to health analysis and guidance. The motion signal may be generated by, for example, one or more accelerometers (e.g., a second sensor 204) included in and/or otherwise operatively coupled to user wearable device 108. The one or more accelerometers may be configured to generate one or more output signals conveying information related to movement and/or motion of a user, for example.

In some implementations, processing circuitry 202 (FIG. 2) and/or a user wearable device application 208 (FIG. 2) may be configured such that the optical signal, the motion signal, and/or other signals can be buffered within a memory (for example, memory 210 in FIG. 2) of the user wearable device(s) 108 for a predetermined time period, and the optical signal and the motion signal can then be provided to other processors for the processing of these signals (for example, processing circuitry 302 of communication device 104 in FIG. 3 or the circuitry of data analysis device(s) 114). As such, power consumption of the user wearable device(s) 108 may be conserved or optimized. Alternatively, in some implementations, the processing circuitry 202 of a user wearable device 108 itself may be used for processing the optical pulse signal and the motion signal.

In some implementations, signal collection or acquisition from an optical sensor (e.g., a sensor 204 shown in FIG. 2) at a 12-50 Hz sampling frequency (for example) may be used. This sampling frequency may be used when there is a general absence of user motion combined with low-levels of perfusion and low ambient light interference and/or at other times. In some implementations, processing circuitry 202 and/or user wearable device application (FIG. 2) are configured to automatically determine (e.g., as described below) the sampling frequency based on various conditions that can affect the output signals from the sensors including, but not limited to, the motion of a user wearing the device 108.

Signal processing challenges caused by user motion may be overcome by adjusting various parameters relating to signal acquisition. For example, optical sensor performance can be adjusted when activity is detected by a motion sensor (e.g., a three-axis accelerometer). In some implementations, if motion above a specific threshold is detected, any or all of the following acquisition parameters of an optical sensor can be adjusted to overcome the level of noise and to improve the accuracy of health characteristic determination: (i) sampling frequency, (ii) LED power, and/or (iii) pulses per sample. Conversely, in some implementations, if motion below a specific threshold is detected, then each of these acquisition parameters may be adjusted to maintain a specific level of performance and measurement precision, while also conserving power.

In the general absence of user motion, a sampling frequency of approximately 20 Hz may be appropriate but, with increased user movement, for example, sampling can be increased to 100 or 200 Hz or, if necessary, up to 1000 Hz or more to ensure that signals are received that are useful for the analysis of user health characteristics.

Various health characteristics of a user may be determined utilizing information in the output signals from sensors discussed herein (e.g., by processing circuitry 202 and/or application 208 of a user wearable device 108 shown in FIG. 2, by processing circuitry 302 and/or application 308 of a communication device 102-106 shown in FIG. 3, by a data analysis device 114, by a server 116, and/or other components of system 100). As one example, sensors associated with a user wearable device 108, such as a smartwatch, may be utilized to determine a user's heart rate, respiration rate, pulse rate variability (PRV), heart rate variability (HRV), and/or other health characteristics. Heart rate is typically described as the number of heartbeats per minute, while HRV and PRV both refer to variability of time intervals between beats. HRV typically refers to variability measurements based on electrocardiography and can be derived from R-R intervals in the standard PQRS waveform. An HRV determination may utilize an ECG sensor (e.g., a user monitoring device 110 and/or 112) on a user that may communicate with wearable device 108. PRV, on the other hand, typically refers to variability determinations based on sensors placed proximal to peripheral arteries, such as optical sensor(s) on a user's wrist that provide a peripheral pulse waveform without the morphology information seen in an ECG signal.

User health characteristics may be determined through signal analysis performed on user wearable device 108 or other components of system 100 such as communication device 102 or data analysis device 114, or the analysis may be performed on more than one component of system 100.

As shown in FIG. 4A, in some implementations, a received signal can be an ECG signal 400, and the time 402 at which each heartbeat has occurred can be determined, for example, from each R spike 402 in the waveform of signal 400. FIG. 4A illustrates an R-R interval 409 (e.g., an amount of time between beats) for reference. Alternatively, the time at which each heartbeat has occurred may be determined from a PPG signal. FIG. 4A also illustrates a sample PPG signal 410 and a sample ECG signal 412 for reference.

As illustrated in FIG. 4B, one method for determining precise heartbeat times from a PPG signal is to determine the maximum points in a PPG gradient plot 450. FIG. 4B illustrates an exemplary method for such detection. In some implementations, processing circuitry 202, wearable device application 208, memory 210, and/or other components may be configured to detect a plurality of heartbeats of the user based on the PPG signal. In some implementations, detecting the plurality of heartbeats comprises detecting the plurality of heartbeats of the user from a maximum gradient of the PPG signal. As shown in FIG. 4B, in some implementations, plot 450 may include an original PPG pulsation signal (e.g., at 30 Hz) 452 and a corresponding gradient 454 of signal 452. Determining heartbeat times from the PPG signal may include determining the locations 456 where gradient 454 is at a maximum. These locations can correspond to individual beats. A heart rate of the user may be determined based on at least the plurality of the determined heartbeats.

Figure 4C:
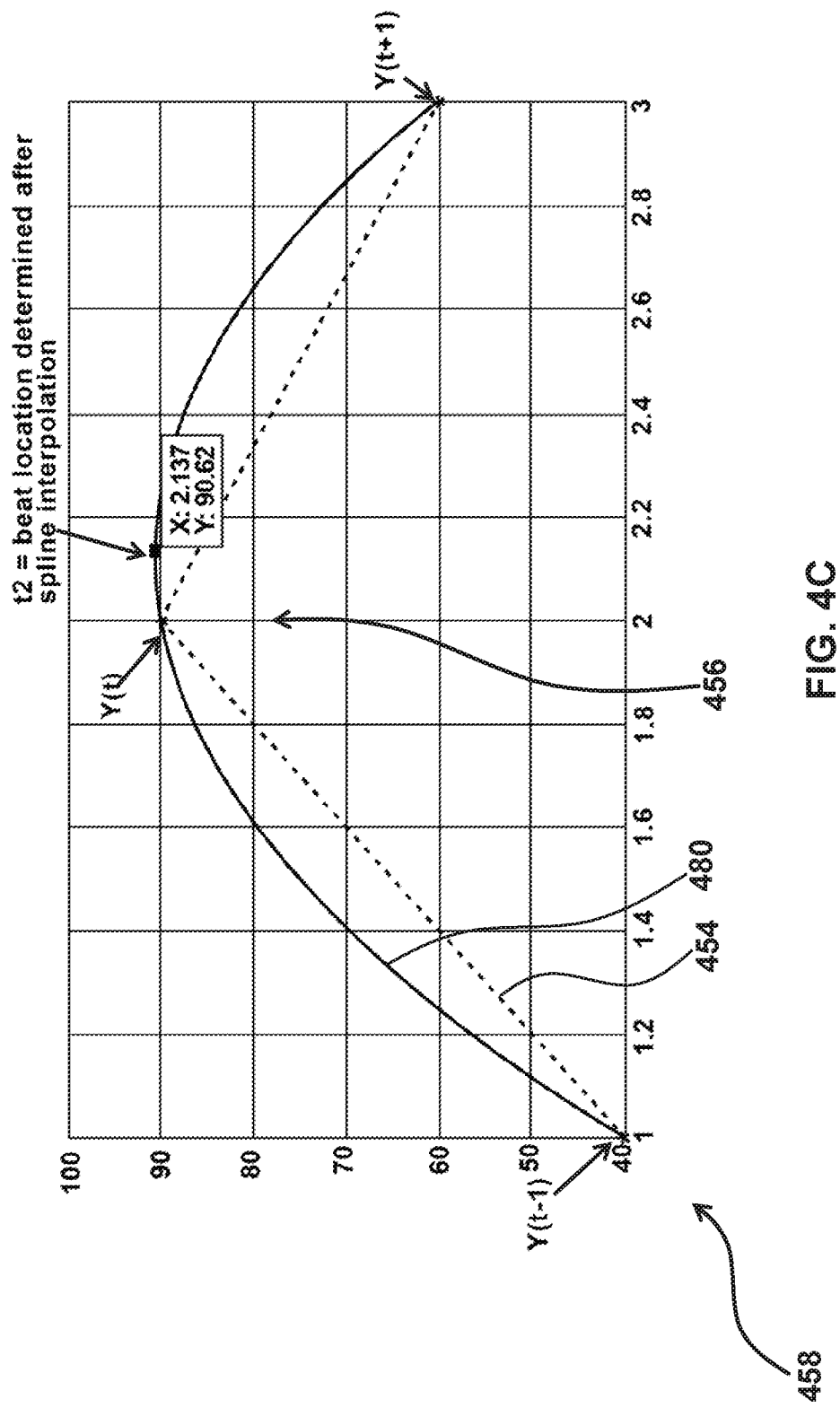
FIG. 4C illustrates an example of spline interpolation in accordance with certain aspects of the present disclosure.

As shown, detecting the plurality of heartbeats may include performing spline interpolation on local maxima of the maximum gradient. For example, the spline interpolation 458 may be performed at individual maximums 456 to accurately determine the timing of a beat. Improved resolution for such heartbeat determinations may be obtained through a variety of methods including, for example, spline interpolation 458 as shown in FIGS. 4B and 4C. As shown in FIG. 4C, a given beat location 456 may be determined based on gradient 454 maximums using a spline interpolation 480. FIG. 4C illustrates, at PPG gradient 454 maximum y(t) 456, spline interpolation 480 for samples y(t−1), y(t), and y(t+1). System 100 (FIG. 1) may be configured such that y(t−1), y(t), and y(t+1) are kept in memory. In this example, if a sampling rate was 25 Hz, time between each sample is 40 ms. Spline interpolation 480 is performed to determine a location of an R spike ($t_2$) with three points of a cubic natural spline.

In certain implementations, system 100 (e.g., via any of the processing and/or data analysis components described above related to FIG. 1-3) may be configured to facilitate a change and/or an adjustment in sampling rate (e.g., by any of the sensors described above) associated with the sensor output signals. In some implementations, the sampling rate may be increased at or near portions of a signal that correspond to a beat (e.g., at or near times that correspond to beat locations 456) and/or decreased in off peak and/or valley areas of plot 450 and/or gradient 454. These changes and/or adjustments in sampling rate may facilitate power and/or data storage space savings.

In some implementations, system 100 (e.g., via any of the processing and/or data analysis components described above related to FIG. 1-3) may be configured to identify noisy portions of a signal and disregard data associated with the noisy portions of the signal. System 100 may be configured to identify the noisy portions of a signal based on information from an accelerometer indicating elevated motion levels, and/or other information. For example, system 100 may be configured to determine that motion levels have breached a motion threshold level and exclude signal data for a period of time when motion levels remain in breach of the motion threshold. The motion threshold level may be determined at manufacture of system 100, determined and/or adjusted by a user (e.g., via a user interface described herein), determined based on prior monitoring of the user, determined based on historical data in medical records associated with the user, and/or may be determined in other ways. In some implementations, responsive to identifying a noisy portion of a signal, system 100 can be configured to perform signal enhancement and/or signal reconstruction operations (e.g., on a PPG sensor signal). After received signals are analyzed, and precise heartbeat times have been determined (for example, over a sample time of 10 seconds), a heart rate in beats per minute can be determined.

Heart rate variability (HRV) and/or pulse rate variability (PRV) may be determined based on the plurality of heartbeats (e.g., determined as described above). In some implementations, PRV and HRV may be described as time variances between successive heartbeats in milliseconds (and/or other increments). Typically, a number of time deltas between beats are determined and then statistical analysis is performed to arrive at various indications of HRV/PRV for the timeframe being examined. This analysis may be done in the time domain, the frequency domain, and the non-linear domain (e.g., by any of the processing and/or data analysis components described above).

Humans breathe (inhale and exhale) anywhere from 6-20 times per minute (or in extreme cases even higher). In some implementations, a user's respiration rate can be determined (e.g., by any of the processing and/or data analysis components described above) from a PPG signal through examination, for example, of the frequency domain, considering slight heart rate increases observed every time a person inhales and slight heart rate decreases every time a person exhales. These small shifts in heart rate, as calculated, for example, through the time delta between successive beats, can be analyzed to determine respiration rate.

In some implementations, system 100 may be configured to analyze a low frequency component of a PPG signal to determine the respiration rate of a user such that the respiration rate of the user may be determined based on the low frequency component of the PPG signal. In some implementations, there exists a low frequency component of the PPG signal that is different than a high frequency component of the PPG signal. The low frequency component of the PPG signal may be related to respiration (e.g., inhalation and exhalation) and the high frequency component of the PPG signal may be related to the plurality of heartbeats. For example, a PPG signal may include a plurality of high frequency individual oscillations (that correspond to individual heartbeats) overlaid on and/or part of a plurality of low frequency oscillations that correspond to respiration. In some implementations, an increasing portion of a given low frequency oscillation may correspond to an inhalation, and a decreasing portion of the given low frequency oscillation may correspond to an exhalation.

Returning to FIG. 1, user characteristics such as those described above can aid the present system in performing various health assessments. For example, on a basic level, a user's resting heart rate, in conjunction with some background information, can be used by system 100 to provide a general assessment of a user's health. Such assessments may be made through calculations on a wearable device 108, a communication device 104, or other devices in system 100.

Subsequent to such health assessments, system 100 may provide guidance to a user through various outputs to a user interface 206 or 306, for example. Such guidance may be in the form of information, or it may provide feedback in a manner designed to alter user behavior, as discussed further below. In addition, system 100 may be configured to provide information to a health professional or other individual, or to store or analyze information in particular databases or servers.

To facilitate health assessments, system 100 can develop a profile for a user that provides a composite characterization of the state of the user's autonomic nervous system (ANS) tone, reflecting the overall influence of sympathetic and parasympathetic nervous systems on the cardiovascular system.

The profile for a user can be established as a baseline, typically prior to the start of an assessment or prolonged measurement. This can include (but is not limited to) facilitation of entry and/or selection of information related to a user's age, gender, height, weight, BMI, and/or other information; determination (e.g., based on the information in the output signals from one or more of the sensors described above) minimum heart rate (if known or previously measured), maximum heart rate (if known or previously measured), HRV statistics in the time domain (e.g., RMSSD—Root Mean Square of the Successive Differences, and pNN50, and the Mean Absolute Deviation can be evaluated to determine the normal range for a user), HRV statistics in the non-linear domain (e.g., Low Frequency Power and High Frequency Power to measure the parameters that effect HRV and the cardiac cycle that usually occur at a frequency lower than heart rate (namely respiration rate)), a determination of whether a user experiences atrial fibrillation, and/or other information.

The parameters for the profile can be received from the user wearable device(s) 108, communication devices 102, 104, and 106, server(s) 116, user monitoring devices 110 and 112, and/or other components of the system 100. For example, personal data such as height, weight, and age of the user can be received from communication device 102, and the blood pressure levels, weight levels, blood glucose levels, etc., can be received from user monitoring devices 110 and 112. Additionally, any historical data of the user (for example, past medical records) can be received from database(s) 118, for example. In some implementations, the server(s) 116 may include database(s) 118 that store user data (for example, historical data of the user, including past medical records) and processor(s) 117 that authenticate user wearable device(s) 108 and communication devices 102, 104, and 106.

Additional parameters for a profile can be derived from a combination of the entered profile information and additional measurement. For example, the Mean Absolute Deviation (MAD) is a calculation of the amount of deviation from the mean heart rate over some predetermined period of time (for example, a day, a week, or a month) indicating an amount of variation in the beat-to-beat intervals (as measured as the time in milliseconds between pulse peaks).

Once real-time user characteristics such as heart rate, HRV, PRV and respiration rate are determined, system 100 is configured to utilize such characteristics to assess various aspects of user's health. For example, by determining relationships between characteristics, system 100 can determine the level of stress experienced by a user. Determining whether the user is in a stressed state may be based on the heart rate, the HRV, the respiration rate, and/or other characteristics of the user. A stressed state may be and/or be related to a condition of the user in which the user is feeling anxious, exasperated, concerned, pressured, tense, and/or otherwise emotionally strained.

In some implementations, determining whether the user is in a stressed state may include determining a particular stress level of the user, which may also be based on the heart rate, HRV, and respiration rate (and/or other characteristics). The stress level may be a value and/or other indicator assigned to an amount of stress felt by the user, and/or an intensity of the stressed state of the user.

A human's autonomic nervous system (ANS) includes two primary components: the sympathetic and the parasympathetic nervous system. When a user experiences physical, mental, or emotional stress, the sympathetic nervous system is stimulated to enable the user to adapt to the stress. Conversely, when an individual experiences a relaxation response (or stress recovery), the parasympathetic nervous system is activated to enable the individual to recover from the stress.

Acute stress may be defined as short periods of intense physiological expression or adaptation to real or perceived threats to a user. Acute stress can be a highly effective response to a threat (for example, enabling fight or flight behaviors) and can be life-preserving. Conversely, chronic stress is a prolonged or habitual state of stress, even after dissipation of a threat. Chronic stress can hyper-activate the inflammatory system and HPA (Hypothalamus Pituitary Axis), causing the sympathetic nervous system (Fight or Flight) to become overactive and inhibit the parasympathetic system (Rest and Digest), which can prevent recovery, an essential part of the healing process.

When the heart rate of a user is measured and HRV or PRV are determined, those values can be compared (e.g., by any of the processing and/or data analysis components described above) to values of the heart rate, respiration rate, HRV/PRV, atrial fibrillation, etc., previously included in the user profile. For example, when the respiration rate/heart rate/HRV/PRV of a user deviates from typical pathological values by a predetermined threshold included in the user profile, system 100 may determine that the user is experiencing a certain level of stress. For example, if a user is experiencing a heart rate of 60 bpm, while their minimum Heart Rate (lowest recorded resting heart rate) is 40 bpm, then 60 bpm may indicate a state of stress with a certain stress level, especially if HRV/PRV is noted to be decreased and respiration rate is unchanged or increased. Conversely, for a user with a minimum heart rate of 56 bpm, a current heart rate of 60 bpm likely means a state of recovery, with a low level of stress. Other parameters may be used to support such assessments.

It should be noted that system 100 is configured to account for pathological irregularities when determining whether a user is experiencing stress. For example, if a user is prone to atrial fibrillation, and this condition is indicated in the user's profile, system 100 is configured to account for (e.g., subtract out the effect of) this pathological atrial fibrillation when making a stress determination. Accounting for other similar pathological irregularities is contemplated.

In addition to determining that a user is experiencing stress, a particular level of the stress can be determined. For example, if a user is currently experiencing a heart rate of 72 bpm though their minimum heart rate (lowest recorded resting heart rate) is 40 bpm, then 72 bpm may indicate a low level of stress. Conversely, if a user is currently experiencing a heart rate of 112 bpm when their minimum heart rate is 40 bpm, then 112 bpm may indicate a high level of stress.

In some implementations, determining whether the user is in a stressed state based on the heart rate, the HRV, the respiration rate, and/or other characteristics can include comprises determining a mathematical model for the user, causing the heart rate, the HRV, the respiration rate, and/or the other characteristics to be used as inputs into the mathematical model, and causing the mathematical model to output the determination of whether the user is in a stressed state based on the inputs. For example, using the profile, a mathematical model can be built (e.g., by any of the processing and/or data analysis components described above), based both on the personal characteristics of the user and population norms for specific physiological functions. Continuing with the example, the normal resting heart rate range (which varies by age and gender) is 55-90 bpm. Maximum heart rate may be calculated as follows: (a) for men over age 30: 207 minus 70% of age, and (b) for women over age 35: 206 minus 88% of age. In other words, a mathematical model can be built based on personal data corresponding to the user and other data corresponding to population norms, and the user's current stress level can be determined based on a comparison of the user's current heart rate, HRV, PRV, and/or respiration rate to the mathematical model. The mathematical model can be updated when the profile is updated with additional data.

In some implementations, stress related determinations can be further responsive to information in output signals from a motion sensor (e.g., an accelerometer as described above) so that determining a stress level may be based on the heart rate, the HRV, the respiration rate and an activity level determined at least in part from a motion sensor. In these types of implementations, the stress determination may also include determination of whether the activity level of the user breaches a minimum activity threshold level, for example, to determine whether the user is awake or asleep. Such minimum activity threshold levels may be determined at the manufacture of system 100, determined and/or adjusted by a user (e.g., using a user interface as described above), determined based on the user profile data for a user, and/or determined in other ways.

In some implementations, the mathematical model can include a weighted combination of heart rate, respiration rate, and heart rate variability for a user. In some implementations, heart rate may be weighted more heavily than respiration rate or heart rate variability.

In some implementations, the weighted combination of heart rate, respiration rate, and heart rate variability can comprise a three feature vector (though other dimensional vectors are contemplated). System 100 may be configured to analyze the features of the vector as they vary (e.g., relative to corresponding thresholds) for a user. Causing the mathematical model to output the determination of whether the user is in a stressed state can include analyzing the three (for example) feature vector in a three (for example) dimensional vector space to determine whether the vector breaches one or more thresholds that define one or more stress zones or volumes in the three dimensional vector space. In this way, the vector may be analyzed in vector space to determine whether a user is stressed and/or to determine a stress level for the user.

These thresholds may be determined based on user profile information and/or other information. The user profile information may describe baseline or normal pathological values for the heart rate, the respiration rate, the HRV, and/or other characteristics of the user. For example, thresholds for individual features (e.g., heart rate, respiration rate, heart rate variability) may be determined. The thresholds may be determined based on the profile information as described above (e.g., based on baseline or normal pathological values (e.g., an overnight heart rate) for individual features for example), real time or near real time information in sensor output signals, and/or other information. The thresholds for individual features may be used in vector space to define one or more stress zones or volumes. The mathematical model may be configured such that, responsive to at least a portion of the (e.g., three) feature vector passing through and/or being bounded by the one or more stress zones, the mathematical model may determine that the user is stressed.

Similarly, the mathematical model may be configured to determine a particular stress level based on a position of the vector relative to one or more of the thresholds, a magnitude and/or length of the vector, and/or other information. For example, the mathematical model may output a length of the vector that is, or is indicative of, the stress level. As another example, the model may output an indication of a relative distance between the vector (or an end of the vector) and one or more of the thresholds that is indicative of the stress level.

The amount of time spent in a sympathetic dominant (stress) state relative to the time spent in a parasympathetic dominant state, for a given timeframe (for example, a day or a week), can be derived from regular measurement of the user's current heart rate, HRV, PRV, and/or respiration rate (e.g., using the mathematical model described above)—allowing the user a key insight into their health and providing an opportunity for intervention if the sympathetic stress state is dominant for too long. This is evident when the net time difference between the two states indicates an on-going net depletion of resources that needs to be replenished (or recovered) through stress management intervention including, for example: structured breathing exercises, meditation, higher quality sleep, and (in most cases other than stress caused by over-training) increased physical activity.

Other lifestyle changes can also enhance recovery and reduce chronic stress. These include, but are not limited to, reduction in caffeine consumption after mid-afternoon, minimizing use of electronics and physical exercise just prior to bed, and improvements in diet by focusing on reductions in sugars and processed food and increases in plant-based foods.

Relative to a user's own cardiovascular and ANS performance, increases in heart rate and respiration rate, accompanied with a decrease in Heart Rate Variability, are a general indication of acute stress. If maintained for prolonged periods of time, this relationship indicates potentially excessive chronic stress. Real-time measurement of these parameters allows for effective intervention to reduce chronic stress and potentially reduce susceptibility to chronic diseases triggered by unmanaged or uncontrolled prolonged periods of chronic stress.

System 100 can be configured to provide graphical displays of information to assist with the assessment of a user's health. For example, operations performed by the a programmable processor (e.g., processing circuitry 202, wearable device application 208, memory 210, and/or other components) may include causing display of information related to the determination of whether a user is in a stressed state on a display of wearable device 108 and/or a different computing device (e.g., communication devices 102-106) associated with the user. In some implementations, the operations can include making multiple individual determinations of whether the user is in a stressed state (e.g., as described above) in an ongoing manner for a period of time. In some implementations, causing display of the information related to the determination of whether the user is in a stressed state can include causing display of information related to the multiple individual determinations of whether the user is in a stressed state. In some implementations, determining whether the user is in a stressed state includes determining an amount of time the user is in the stressed state during the period of time.

Figure 5:
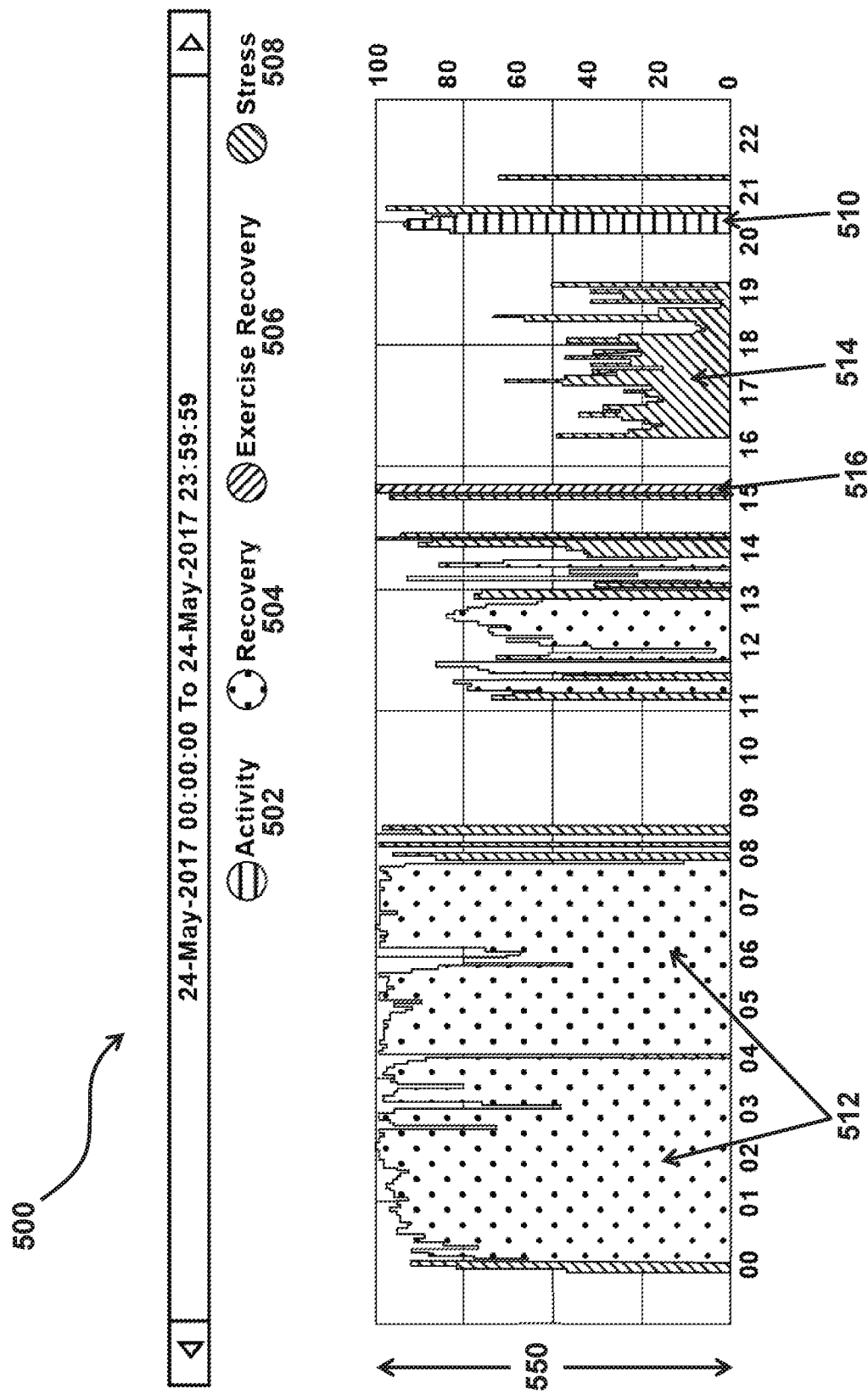
FIG. 5 illustrates an exemplary display of a user's health states over time, utilizing HRV calculations in accordance with certain aspects of the present disclosure.

An example of a display utilizing a user's health and/or activity states over time is illustrated in FIG. 5. FIG. 5 illustrates display 500 for a hypothetical period of time for a user. In this example, measurements were taken and calculations made (as described herein) throughout the day (e.g., from 00:00:00 to 23:59:59). In some implementations, the operations performed by the at least one programmable processor (e.g., processing circuitry 202, wearable device application 208, memory 210, and/or other components) can include determining whether an activity level is indicative of sleep, exercise, and/or normal daily activity; and causing the display of periods of stress, sleep, exercise, and/or normal daily activity. For example, exemplary display 500 in FIG. 5 indicates health and/or activity states including "Activity" 502, "Recovery" 504, "Exercise Recovery" 506, and "Stress" 508. Specifically, display 500 illustrates: activity 510 (for example, from 8 pm to 9 pm), recovery 512 (for example, from midnight to 8 am), stress 514 (for example, from 4 pm to 7 pm), and exercise recovery 516 at about 3 pm. From midnight to 8 am, display 500 of FIG. 5 illustrates mostly a recovery state. From 11 am to 3 pm, display 500 illustrates mixed stress and recovery states throughout the workday; from 4 pm to 7 pm, display 500 of FIG. 5 illustrates low-to-mid level stress intensity (for example, because of a marathon phone conference); and from 8 pm to 9 pm, display 500 illustrates an exercise activity (for example, exercising on an elliptical trainer at the gym).

In one implementation, the amplitude of the states shown in display 500 of FIG. 5 may be calculated as proportional to the inverse of the current heart rate minus the minimum heart rate (for a given user), amplified or reduced by the degree of HRV and the rate of respiration for the user. As the current heart rate nears the minimum, and HRV and respiration rate are appropriate for recovery, the amplitude will approach the maximum. The converse would be true for an exemplary stress amplitude calculation.

At night, primarily during sleep, heart rate and respiration rate are lowered and HRV (or similarly PRV) increases relative to periods of daytime stress. Even during the night, however, movement or wakefulness can be detected, and recorded for review by the user. This can provide insight into both the quantity (amount of time) and quality (amount of recovery) of sleep. Unmanaged chronic stress can cause reductions in both the quantity and the quality of sleep. The deeper a user's relaxation during sleep, the higher the level of recovery will be indicated.

Accelerometer data can be examined to determine if the user is active and, if so, can be used to determine an activity intensity value. If the patient is not active, then system 100 may determine if the user is in recovery based on factors such as a lower heart rate, an increased HRV/PRV, and a reduced respiration rate (relative to the patient's normal ranges for each). If the user is not active and not in recovery, system 100 can determine that the user is in a state of stress.

In one example, a user may be determined to be in recovery if he has a minimum heart rate of 47, is currently experiencing a heart rate of 50, while not being active, and demonstrates increased heart rate variability and a reduced respiration rate. As described above, in this example, the amplitude of the recovery indication in a health state graph such as FIG. 5 may be calculated as proportional to the inverse of the current heart rate minus the minimum heart rate amplified or reduced by the degree of HRV and rate of respiration for the person. As the current heart rate nears the minimum, and HRV and respiration rate are appropriate for recovery, the amplitude will approach the maximum. The converse would be true for an exemplary stress amplitude calculation.

System 100 can be configured to display various health assessment data gathered and/or calculated, as previously described. For example, timelines of health assessment data may be displayed on wearable device 108, or communication device 102, through their respective wearable device application 208 or communication device application 308 (see, e.g., FIGS. 6A-6E).

For example, as shown in FIG. 6A, a view 600 of health assessment data may be displayed on wearable device 108. Similar to display 500 shown in FIG. 5, view 600 comprises a visual indication of recent periods of stress 602 and non-stress 604. FIG. 6B illustrates a daily summary view 610 for a busy Thursday workday (for example). View 610 includes an indication of sleep quality 612, a percentage of the day that stress levels were high 614, and a timeline that displays heath and/or activity state by time of day 616.

FIG. 6C illustrates an example view 620 of health assessment data that includes an annotated timeline 622 of health and/or activity states. Annotated timeline 622 indicates when a user was in states of stress 624, recovery 626, physical activity 628, and light physical activity 630. Annotated timeline 622 can be overlaid with a heart rate indication 632 for the user. Annotations on annotated timeline 622 can include advice and/or summary windows 634 that provide advice and/or activity summaries to the user, and time stamp graphics 636 or messages 638 that indicate various events.

Figure 6D:
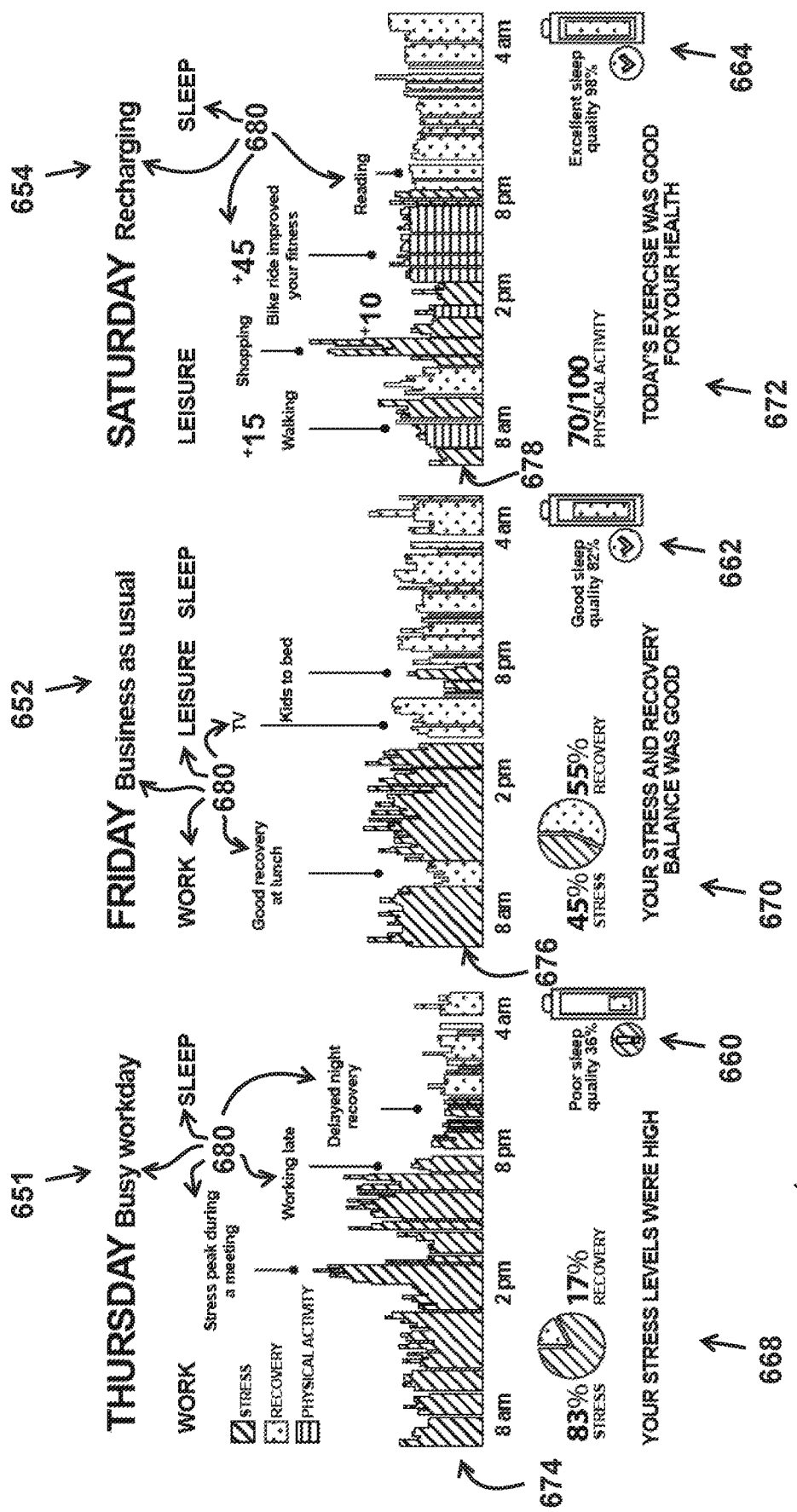
FIG. 6D illustrates a fourth example of a health information display of a user wearable device application and/or a communication device application in accordance with certain aspects of the present disclosure.

FIG. 6D illustrates a multi-day summary view 650 for three successive days (Thursday, Friday, Saturday). View 650 includes a view 651 similar to view 610 described above, and additional similar views 652 and 654 for Friday and Saturday. Views 651, 652, and 654 include indications of sleep quality 660, 662, 664, percentages of the day that stress levels were high 668, 670, 672, and annotated timelines 674, 676, 678, that display heath and/or activity state by time of day, along with summary and/or advice windows 680 (e.g., similar to those shown in FIG. 6C).

Figure 6E:
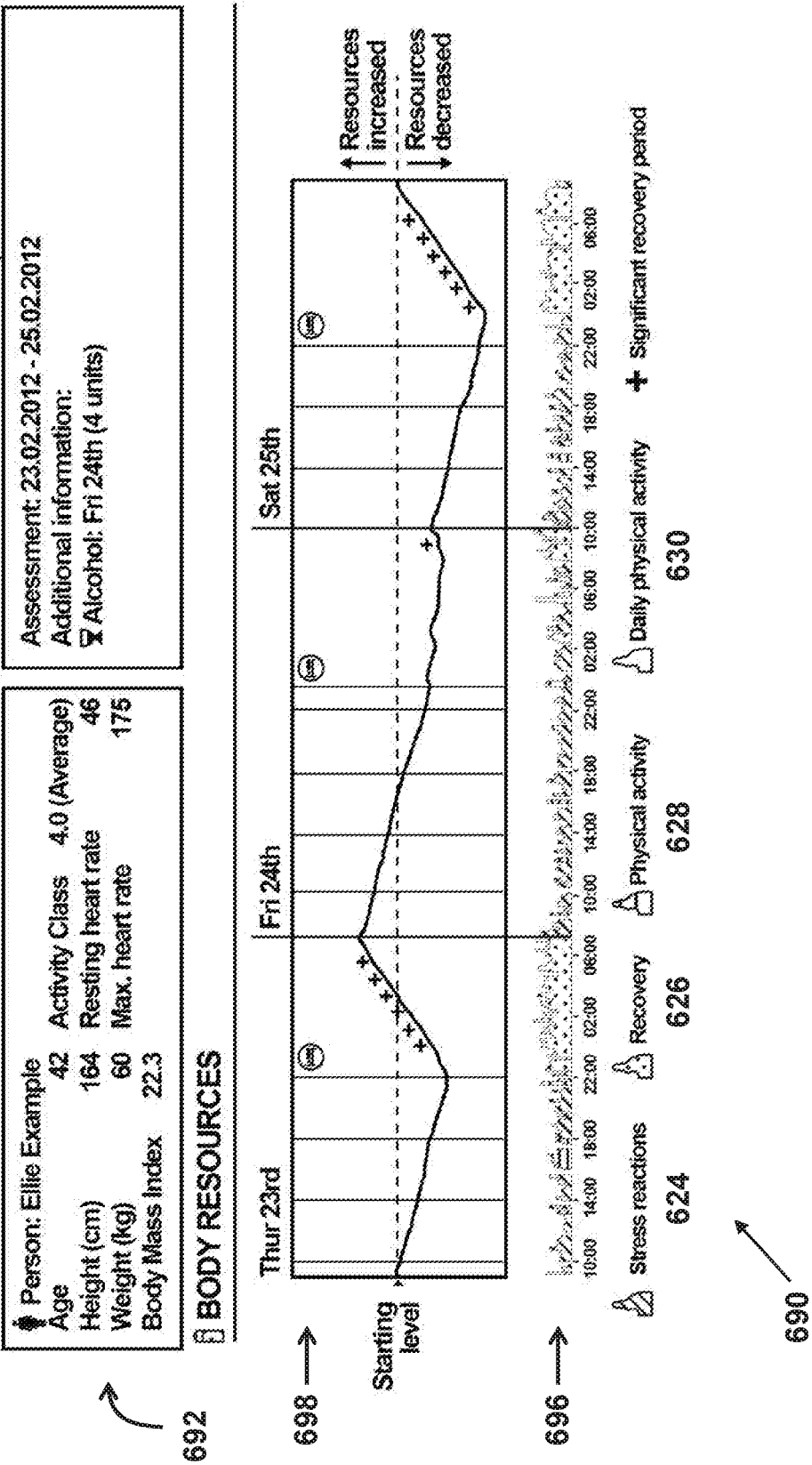
FIG. 6E illustrates a fifth example of a health information display of a user wearable device application and/or a communication device application in accordance with certain aspects of the present disclosure.

FIG. 6E illustrates a lifestyle assessment summary view 690. View 690 includes a user characteristics summary portion 692, additional information 694, a timeline 696 that indicates when a user was in states of stress 624, recovery 626, physical activity 628, and light physical activity 630. View 690 also illustrates a body resources portion 698 indicating whether the user's body resources increased or decreased over a period of three days.

In one implementation, the user wearable device application 208 can be programmed to update a stress/recovery/sleep/activity timeline on a beat by beat basis to ensure that it displays immediate health assessment information both on demand as requested by the user, and when actionable information is detected. Actionable information may include the detection of specific stress events that would benefit from interventions or the detection and display of activity or recovery events that can re-enforce positive behavior performed by a user. The wearable device 108 may also be programmed to trigger haptic feedback to the user in the form of a mild vibration along with a concise message suggesting actions the user may perform depending on the type of detected event.

System 100 can be configured to provide additional, more detailed information on a communication device 102 (e.g., a mobile phone or computer), for example. In one example, illustrated in FIG. 6B, communication device 102 may display a detailed health state graph for a particular day. Such a display may indicate varying user states such as stress, recovery and physical activity in different colors on a bar graph and may indicate the percentage of the day spent in each state to allow a user to understand just how taxing a particular day may have been on his or her body.

The exemplary display of FIG. 6B illustrates that periods of recovery, stress or physical activity can be denoted by different colored columns (e.g., green, red and blue) or shading patterns, respectively. In addition to color-coded and/or shaded bar charts, additional assessment information can be provided in the display, for example, warnings regarding poor sleep quality/duration can be given, as well as positive feedback relating to exercise.

FIG. 6C illustrates an additional exemplary display including more detailed information. Heart rate throughout the day can be displayed, as well as indications of light or strenuous physical activity and commentary regarding the health effects of various states observed during the day. In addition, icons such as a suitcase or a bed, along with corresponding bars across the time axis, can be displayed as the result of user-entered journaling of activities. For example, a suitcase may indicate a commute to or from work, and a bed may indicate sleep.

FIG. 6D illustrates an additional exemplary display showing a user how his or her body has been affected by activities over a number of days. In addition to bar charts showing the user's states throughout a few days and nights, additional indications can be provided regarding percentages of stress versus recovery state, sleep quality and exercise activity.

FIG. 6E illustrates an additional exemplary display showing an overall assessment of a user's body resources over time, indicating periods of resource depletion and resource recovery—and showing a cumulative state over time that may be determined by summation of the additive values of recovery, less the subtractive values of stress.

In some implementations, the operations performed by the at least one programmable processor (e.g., processing circuitry 202, wearable device application 208, memory 210, and/or other components) may include generating and causing display of a recommendation for lifestyle changes determined by the amount of time the user is in the stressed state and/or other information. In some implementations, the operations performed by the a processor can further include, responsive to a determination that the user is in a stressed state, determining breathing guidance and causing display of the breathing guidance to the user on the display of a wearable device to facilitate stress reduction.

For example, system 100 may be designed to alert a user to specific events, for example, with haptic feedback through wearable device 108. In one example, an alert may be given when a period of high stress is observed. After such an alert, health-related guidance may be given to the user, such as breathing guidance.

An effective intervention to reduce stress and potentially reduce susceptibility to chronic diseases is to optimize breathing during periods of prolonged stress. An optimal respiration rate for an average person not currently experiencing respiratory health issues can be considered less than 10 breaths per minute, although this level can be personalized given respiration patterns and health conditions of a particular user.

Breathing guidance can be displayed to a user via a display on a user wearable device 108 or a display of communication device 102. The breathing guidance can be presented to the user in real-time as needed or presented on-demand. For example, when system 100 determines that the user's stress level is above a predetermined threshold for a prolonged period of time, the system can provide breathing guidance to the user. Alternatively, the user and/or a medical professional can request that breathing guidance be provided at predetermined intervals of time.

Figure 7:
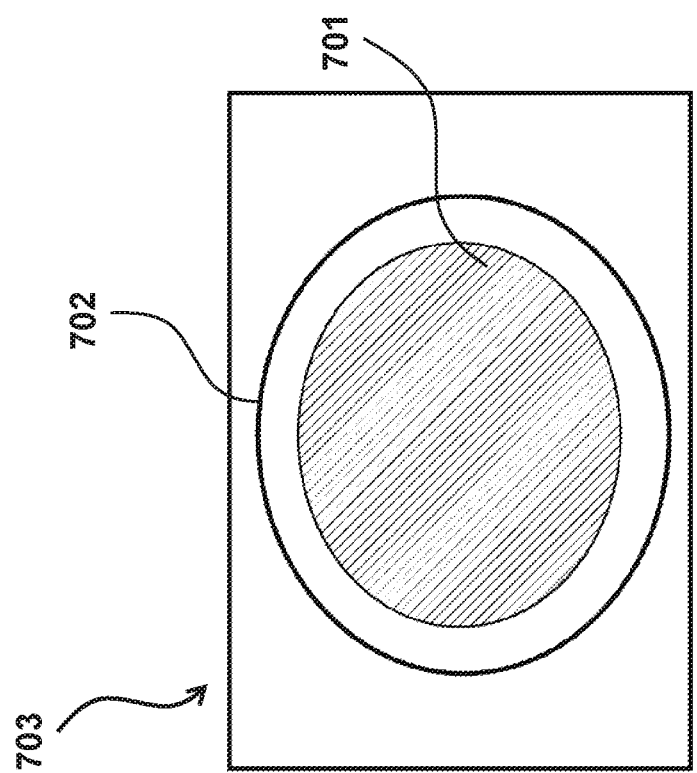
FIG. 7 illustrates an exemplary display that may be used to guide a user's breathing rate in accordance with certain aspects of the present disclosure.

Components of system 100 (for example, the display on wearable device 108) can be configured to display graphical breathing guidance to user. FIG. 7 illustrates a simple exemplary display 703 that may be shown on wearable device 108. Such a display can be synchronized to a user's breath, or to a desired reduced breathing rate. In the example shown in FIG. 7, inner circular shape 701 may expand and/or contract in diameter relative to outer circular shape 702 to indicate to the user when to breath in and/or out for example. This exemplary display is not intended to be limiting.

In some implementations, a user's PRV and/or HRV, baseline pathological (e.g., user profile) information, and/or other information can be used to determine an optimal breathing rate for the user in view of the user's current respiration rate. When activated through a set of programmable triggers or manually activated by the user, breathing guidance can be determined based on the current breathing rate of the user (e.g., as determined from the user's respiration rate derived through frequency domain analysis of PRV statistics as measured from an optical sensor). System 100 can then be programmed to select, as breathing guidance, a breathing rate that is slightly slower (e.g., 1-2 breaths per minute slower) than the current respiration rate. The user's heart rate and HRV/PRV are continuously monitored throughout the breathing guidance and, as the intensity of the current stress level of the user is reduced, the breathing guidance can further reduce the desired breaths per minute until either a) breaths per minute is less than 10, or b) heart rate and/or HRV/PRV are reduced appropriately.

Given that the respiration rate, heart rate, HRV and PRV are being monitored, the effectiveness of the breathing exercise can be determined. Ideally, there is a positive and quantifiable change in heart rate, respiration rate, and HRV/PRV during the breathing exercises. If the exercise is not effective in altering these parameters, the amount of time inhaling or exhaling can be increased or modified, along with guidance on the optimal inhalation and exhalation techniques. This may prevent instances of over breathing, which may inhibit the desired relaxation effect of the breathing exercise.

Using such methods, system 100 can assess both the effectiveness of breathing exercises, and present feedback to the user performing the exercise, so he or she can see the immediate effect of the exercise on their current level of stress and physiology. In some implementations, system 100 can be configured to cause display of a goal respiration rate and a current respiration rate on a continuum. In other implementations, system 100 can be configured to cause display of individual goal/actual inhalation times and/or goal/actual exhalation times. This provides a positive feedback mechanism that may encourage the user to continue the exercise, as they can directly and quantifiably see the effect on their physiology, and it may therefore help to develop an effective tool for stress management. When a user observes (or is alerted) to the occurrence of prolonged periods of stress, the user can immediately remedy with breathing intervention methods to reduce stress, potentially preventing deterioration of health, and enhancing wellbeing.

Although a few embodiments have been described in detail above, other modifications are possible. The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, modules, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a touch screen, a cathode ray tube (CRT), or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and sub combinations of the disclosed features and/or combinations and sub combinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A computer program product comprising a non-transitory, machine-readable medium storing instructions which, when executed by at least one programmable processor, cause the at least one programmable processor to perform operations comprising:
    receiving, at the at least one programmable processor, a photoplethysmographic (PPG) signal communicated by a PPG sensor of a wearable device worn by a user;
    detecting a plurality of heartbeats of the user based on the PPG-signal;
    determining a heart rate of the user based on at least the plurality of heartbeats;
    determining a heart rate variability (HRV) of the user based on the plurality of heartbeats;
    determining a respiration rate of the user based on a low frequency component of the PPG signal; and
    determining whether the user is in a stressed state based on the heart rate, the HRV, and the respiration rate, wherein determining whether the user is in a stressed state based on the heart rate, the HRV, and the respiration rate comprises determining a mathematical model for the user, causing the heart rate, the HRV, and the respiration rate to be used as inputs into the mathematical model, and causing the mathematical model to output the determination of whether the user is in a stressed state based on the inputs, wherein the mathematical model comprises a weighted combination of the heart rate, the respiration rate, and the HRV for the user, wherein the heart rate is weighted more heavily than the respiration rate or the HRV.

2. The computer program product of claim 1, wherein the detecting the plurality of heartbeats comprises detecting the plurality of heartbeats of the user from a maximum gradient of the PPG signal.

3. The computer program product of claim 2, wherein detecting the plurality of heartbeats further comprises performing spline interpolation on local maxima of the maximum gradient.

4. The computer program product of claim 1, wherein determining whether the user is in a stressed state based on the heart rate, the HRV, and the respiration rate comprises determining a stress level of the user based on the heart rate, the HRV, and the respiration rate.

5. The computer program product of claim 1, wherein the weighted combination of heart rate, respiration rate, and heart rate variability comprises a three feature vector, and causing the mathematical model to output the determination of whether the user is in a stressed state comprises analyzing the three feature vector in a three dimensional vector space to determine whether the three feature vector breaches one or more thresholds that define one or more stress zones or volumes in the three dimensional vector space, the mathematical model configured such that, responsive to at least a portion of the three feature vector passing through and/or being bounded by the one or more stress zones or volumes, the mathematical model determines that the user is in a stressed state.

6. The computer program product of claim 5, wherein the thresholds are determined based on user profile information, the user profile information describing baseline or normal pathological values for the heart rate, the respiration rate, and the HRV of the user.

7. The computer program product of claim 1, wherein the operations performed by the at least one programmable processor further comprise receiving, at the at least one programmable processor, a motion signal communicated by an accelerometer sensor of the wearable device worn by the user, the motion signal conveying information related to an activity level of the user; and,
    wherein determining whether the user is in a stressed state is further based on the activity level.

8. The computer program product of claim 7, wherein determining whether the user is in a stressed state includes a determination of whether the activity level of the user breaches a minimum activity threshold level.

9. The computer program product of claim 1, wherein the operations performed by the at least one programmable processor further comprise causing display of information related to the determination of whether the user is in a stressed state on a display of the wearable device and/or a different computing device associated with the user.

10. The computer program product of claim 9, wherein the operations performed by the at least one programmable processor further comprise making multiple determinations of whether the user is in a stressed state over a period of time, and
    wherein the causing display of information related to the determination of whether the user is in a stressed state comprises causing display of information related to the multiple determinations of whether the user is in a stressed state.

11. The computer program product of claim 10, wherein the operations performed by the at least one programmable processor further comprise determining an amount of time the user is in the stressed state during the period of time.

12. The computer program product of claim 11, wherein the operations performed by the at least one programmable processor further comprise generating and causing display of a recommendation for lifestyle changes determined based on the amount of time the user is in the stressed state.

13. The computer program product of claim 1, wherein the operations performed by the at least one programmable processor further comprise receiving, at the at least one programmable processor, a motion signal communicated by an accelerometer sensor of the wearable device worn by a user during a period of time, the motion signal conveying information related to an activity level of the user.

14. The computer program product of claim 13, wherein the operations performed by the at least one programmable processor further comprise:
    determining whether the activity level is indicative of sleep, exercise, and/or normal daily activity; and
    causing display of periods of stress, sleep, exercise, and/or normal daily activity during the period of time.

15. The computer program product of claim 1, wherein the operations performed by the at least one programmable processor further comprise, responsive to a determination that the user is in a stressed state, determining breathing guidance and causing display of the breathing guidance to the user on a display of the wearable device to facilitate stress reduction.

16. A wrist worn device configured to determine whether a user is in a stressed state, the wrist worn device comprising:
    a photoplethysmographic (PPG) sensor configured to generate a PPG signal;
    at least one programmable processor and a non-transitory, machine-readable medium storing instructions which, when executed by the at least one programmable processor, cause the at least one programmable processor to perform operations comprising:
    receiving, at the at least one programmable processor, the PPG signal communicated by the PPG sensor;
    detecting a plurality of heartbeats of the user based on the PPG-signal;
    determining a heart rate of the user based on at least the plurality of heartbeats;
    determining a heart rate variability (HRV) of the user based on the plurality of heartbeats;
    determining a respiration rate of the user based on a low frequency component of the PPG signal; and
    determining whether the user is in a stressed state based on the heart rate, the HRV, and the respiration rate, wherein determining whether the user is in a stressed state based on the heart rate, the HRV, and the respiration rate comprises determining a mathematical model for the user, causing the heart rate, the HRV, and the respiration rate to be used as inputs into the mathematical model, and causing the mathematical model to output the determination of whether the user is in a stressed state based on the inputs, wherein the mathematical model comprises a weighted combination of the heart rate, the respiration rate, and the HRV for the user, wherein the heart rate is weighted more heavily than the respiration rate or the HRV; and
    a user interface controlled by the at least one programmable processor, the user interface controlled by the at least one programmable processor to display information related to the determination of whether the user is in a stressed state.

17. The wrist worn device of claim 16, wherein the detecting the plurality of heartbeats comprises detecting the plurality of heartbeats of the user from a maximum gradient of the PPG signal.

18. The wrist worn device of claim 17, wherein detecting the plurality of heartbeats further comprises performing spline interpolation on local maxima of the maximum gradient.

19. The wrist worn device of claim 16, wherein determining whether the user is in a stressed state based on the heart rate, the HRV, and the respiration rate comprises determining a stress level of the user based on the heart rate, the HRV, and the respiration rate.

20. The wrist worn device of claim 16, wherein the weighted combination of heart rate, respiration rate, and heart rate variability comprises a three feature vector, and causing the mathematical model to output the determination of whether the user is in a stressed state comprises analyzing the three feature vector in a three dimensional vector space to determine whether the three feature vector breaches one or more thresholds that define one or more stress zones or volumes in the three dimensional vector space, the mathematical model configured such that, responsive to at least a portion of the three feature vector passing through and/or being bounded by the one or more stress zones or volumes, the mathematical model determines that the user is in a stressed state.

21. The wrist worn device of claim 20, wherein the thresholds are determined based on user profile information, the user profile information describing baseline or normal pathological values for the heart rate, the respiration rate, and the HRV of the user.

22. The wrist worn device of claim 16, wherein the operations performed by the at least one programmable processor further comprise receiving, at the at least one programmable processor, a motion signal communicated by an accelerometer sensor of the wearable device worn by the user, the motion signal conveying information related to an activity level of the user; and,
    wherein determining whether the user is in a stressed state is further based on the activity level.

23. The wrist worn device of claim 22, wherein determining whether the user is in a stressed state includes a determination of whether the activity level of the user breaches a minimum activity threshold level.

24. The wrist worn device of claim 16, wherein the operations performed by the at least one programmable processor further comprise causing display of information related to the determination of whether the user is in a stressed state on a display of the wearable device and/or a different computing device associated with the user.

25. The wrist worn device of claim 24, wherein the operations performed by the at least one programmable processor further comprise making multiple determinations of whether the user is in a stressed state over a period of time, and
    wherein the causing display of information related to the determination of whether the user is in a stressed state comprises causing display of information related to the multiple determinations of whether the user is in a stressed state.

26. The wrist worn device of claim 25, wherein the operations performed by the at least one programmable processor further comprise determining an amount of time the user is in the stressed state during the period of time.

27. The wrist worn device of claim 26, wherein the operations performed by the at least one programmable processor further comprise generating and causing display of a recommendation for lifestyle changes determined based on the amount of time the user is in the stressed state.

28. The wrist worn device of claim 16, wherein the operations performed by the at least one programmable processor further comprise receiving, at the at least one programmable processor, a motion signal communicated by an accelerometer sensor of the wearable device worn by a user during a period of time, the motion signal conveying information related to an activity level of the user.

29. The wrist worn device of claim 28, wherein the operations performed by the at least one programmable processor further comprise:
    determining whether the activity level is indicative of sleep, exercise, and/or normal daily activity; and
    causing display of periods of stress, sleep, exercise, and/or normal daily activity during the period of time.

30. The wrist worn device of claim 16, wherein the operations performed by the at least one programmable processor further comprise, responsive to a determination that the user is in a stressed state, determining breathing guidance and causing display of the breathing guidance to the user on the display of a wearable device to facilitate stress reduction.

31. A method for determining whether a user of a wearable device is in a stressed state, the method comprising:
receiving, with at least one programmable processor, a photoplethysmographic (PPG) signal communicated by a PPG sensor of the wearable device worn by the user;
detecting a plurality of heartbeats of the user based on the PPG-signal;
determining a heart rate of the user based on at least the plurality of heartbeats;
determining a heart rate variability (HRV) of the user based on the plurality of heartbeats;
determining a respiration rate of the user based on a low frequency component of the PPG signal; and
determining whether the user is in a stressed state based on the heart rate, the HRV, and the respiration rate, wherein determining whether the user is in a stressed state based on the heart rate, the HRV, and the respiration rate comprises determining a mathematical model for the user, causing the heart rate, the HRV, and the respiration rate to be used as inputs into the mathematical model, and causing the mathematical model to output the determination of whether the user is in a stressed state based on the inputs, wherein the mathematical model comprises a weighted combination of the heart rate, the respiration rate, and the HRV for the user, wherein the heart rate is weighted more heavily than the respiration rate or the HRV.

32. The method of claim 31, wherein the detecting the plurality of heartbeats comprises detecting the plurality of heartbeats of the user from a maximum gradient of the PPG signal.

33. The method of claim 32, wherein detecting the plurality of heartbeats further comprises performing spline interpolation on local maxima of the maximum gradient.

34. The method of claim 31, wherein the weighted combination of heart rate, respiration rate, and heart rate variability comprises a three feature vector, and causing the mathematical model to output the determination of whether the user is in a stressed state comprises analyzing the three feature vector in a three dimensional vector space to determine whether the three feature vector breaches one or more thresholds that define one or more stress zones or volumes in the three dimensional vector space, the mathematical model configured such that, responsive to at least a portion of the three feature vector passing through and/or being bounded by the one or more stress zones or volumes, the mathematical model determines that the user is in a stressed state.

* * * * *